(12) United States Patent
Mayer et al.

(10) Patent No.: US 12,408,830 B2
(45) Date of Patent: Sep. 9, 2025

(54) ILLUMINATION SYSTEM

(71) Applicant: HOYA CORPORATION, Tokyo (JP)

(72) Inventors: Wolfgang Mayer, Friedberg (DE); Kunihiko Onobori, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 380 days.

(21) Appl. No.: 18/023,052

(22) PCT Filed: Aug. 19, 2021

(86) PCT No.: PCT/IB2021/057630
§ 371 (c)(1),
(2) Date: Feb. 24, 2023

(87) PCT Pub. No.: WO2022/043836
PCT Pub. Date: Mar. 3, 2022

(65) Prior Publication Data
US 2023/0389786 A1    Dec. 7, 2023

(30) Foreign Application Priority Data

Aug. 26, 2020 (DE) ..................... 10 2020 122 282.3

(51) Int. Cl.
*A61B 1/06* (2006.01)
*A61B 1/04* (2006.01)

(52) U.S. Cl.
CPC .......... *A61B 1/0638* (2013.01); *A61B 1/0676* (2013.01); *A61B 1/0684* (2013.01); *A61B 1/041* (2013.01)

(58) Field of Classification Search
CPC ... A61B 1/0638; A61B 1/0646; A61B 1/0676; A61B 1/0684
See application file for complete search history.

(56) References Cited

U.S. PATENT DOCUMENTS 8,840,267 B2   9/2014  Li et al.
10,517,473 B2  12/2019 Fujiwara
(Continued)

FOREIGN PATENT DOCUMENTS

DE   11 2018 003134 T5   3/2020
JP   2009-086057 A       4/2009
(Continued)

OTHER PUBLICATIONS

International Search Report issued in International Bureau of WIPO Patent Application No. PCT/IB2021/057630, dated Oct. 29, 2021, along with an English translation thereof.
(Continued)

*Primary Examiner* — Alexander K Garlen
(74) *Attorney, Agent, or Firm* — GREENBLUM & BERNSTEIN, P.L.C.

(57) ABSTRACT

It is provided an illumination apparatus, comprising a beam combiner comprising two dichroic reflective surfaces and configured to combine a first light from a first light source, a second light from a second light source, and a third light from a third light source into combined light; a combination of the second light passing through the combiner and the third light passing through the combiner is closer to the white point than each of the second light and the first light passing through the combining portion; or the third light passing through the combiner is closer to the white point than each of the second light and the first light passing through the combining portion.

8 Claims, 8 Drawing Sheets

(56) References Cited

U.S. PATENT DOCUMENTS

| | | |
|---|---|---|
| 11,559,194 B2 | 1/2023 | Onobori |
| 2005/0190562 A1* | 9/2005 | Keuper ............... H04N 9/3144 362/555 |
| 2005/0270775 A1* | 12/2005 | Harbers ............... H04N 9/315 257/E33.071 |
| 2008/0246920 A1* | 10/2008 | Buczek ............... A61B 1/0655 351/221 |
| 2010/0280322 A1 | 11/2010 | Mizuyoshi |
| 2011/0149246 A1* | 6/2011 | Artsyukhovich .... A61B 3/0008 351/221 |
| 2012/0271103 A1* | 10/2012 | Gono ................ A61B 1/0655 600/109 |
| 2013/0100639 A1 | 4/2013 | Li et al. |
| 2013/0113911 A1 | 5/2013 | Hanano et al. |
| 2019/0235369 A1 | 8/2019 | Janssens |
| 2021/0076921 A1 | 3/2021 | Nagae et al. |

FOREIGN PATENT DOCUMENTS

| | | |
|---|---|---|
| JP | 2016-022043 A | 2/2016 |
| WO | 2011/017062 A1 | 2/2011 |
| WO | 2018/051558 A1 | 3/2018 |
| WO | WO2019/198553 A1 | 10/2019 |

OTHER PUBLICATIONS

Office Action in European application No. 21762122.6, dated Jan. 31, 2024.

Notice of Reasons for Refusal issued in Japanese Patent Application No. 2023-507351, dated Dec. 5, 2023, along with an English translation thereof.

\* cited by examiner

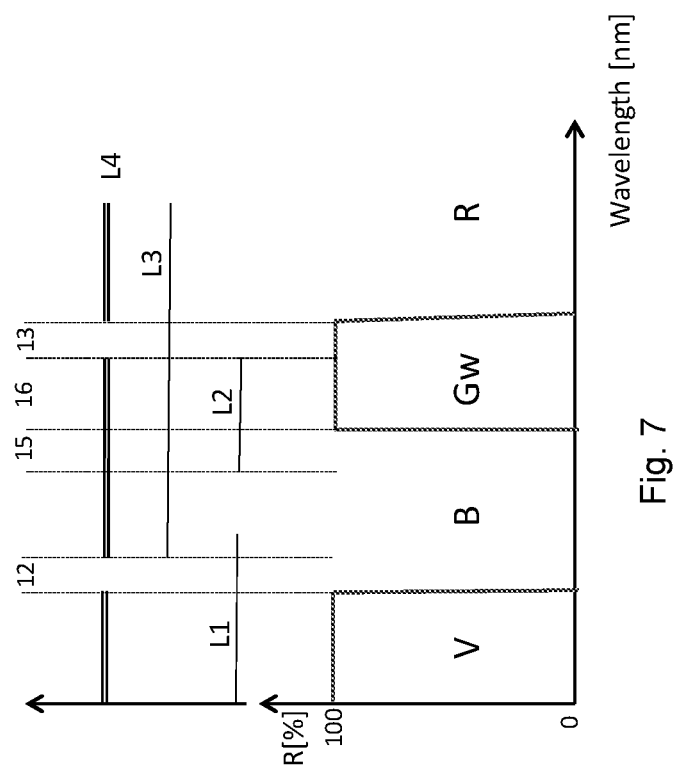

Phosphor covered white light LED with dome reflector lens

Phosphor covered white light LED

ILLUMINATION SYSTEM

FIELD OF THE INVENTION

The present application relates to an illumination system. In particular, it relates to an illumination system for an endoscope enabling both white light illumination and narrowband (colored) illumination by two different colors such as vascular pattern enhanced illumination.

Abbreviations

B blue
CIE Commission internationale de l'éclairage
G green
Gw Green wide
Hb Haemoglobin
HbO2 oxygenated Haemoglobin
LED Light Emitting Diode
R red
V violet
WL White Light
WLI White Light Illumination

BACKGROUND OF THE INVENTION

White Light (WL) and Vascular pattern enhanced illumination (so called narrowband illumination which has illumination spectrum synchronized to hemoglobin absorption spectrum) are getting more common for endoscopic imaging. FIG. 1 shows the absorption spectra of Hb (haemoglobin, i.e. Desoxyhaemoglobin) and HbO2 (oxygenated haemoglobin, i.e. Oxyhaemoglobin), taken from JP 2016-022043 A. E1-E8 are isosbestic points of Hb and HbO2, i.e. wavelength at which the absorption of Hb is the same as the absorption of HbO2 (E8 is a quasi-isoabsorbing point). In other words, the absorption at the isosbestic points is independent from the level of oxygenation of the haemoglobin. W0 to W7 and WR denote the wavelength ranges between two adjacent isosbestic points and beyond the isosbestic point E8, respectively.

Accordingly, in conventional vascular imaging, a tissue is illuminated with a spectrum as schematically shown in FIG. 2. The spectrum comprises violet light V and/or green wide light Gw. Green-wide light includes bluish green to red wavelengths. These lights include substantially at least one of the wavelength ranges W0, W1 (for V light) and W5 (for Gw light). In these wavelength ranges, there is a large difference in absorption between Hb and HbO2. Thus, the intensity of the absorbed light differs strongly between tissue comprising Hb and tissue comprising HbO2. The green wide light Gw is also used to observe the tissue optically. Since it may have a broad spectral distribution, the Gw light has a green hue. Typically, the emission spectra of V light and Gw light do not overlap.

In endoscopy, in order to simplify the system and to enable compatibility with many different types of endoscopes, the light source may be arranged in an external box (light source box or processor system). The light from the external box may be guided from the proximal end of the endoscope to the distal end of the endoscope through one or more optical fibers in order to illuminate an object space of an objective lens arranged at the distal end of the endoscope.

CIE 1931 links between distributions of wavelengths in the electromagnetic visible spectrum and physiologically perceived colors in human color vision. FIG. 3 shows a gamut according to CIE1931 (x-y-plane, taken from people.cs.clemson.edu). The area in the middle (without color notations) denotes whitish light. The number at the border of the gamut indicate the wavelength (in nm) of the respective spectral clean light. White light has the coordinates x=⅓; y=⅓; and z=⅓.

SUMMARY OF THE INVENTION

The present invention provides an improved illumination system allowing larger flexibility between WLI and narrow band illumination.

It is provided an illumination apparatus, comprising a beam combiner comprising first, second, and third inputs, a combining portion, and an output; wherein the combining portion is configured to combine a first light inputted from the first input into the combining portion, a second light inputted from the second input into the combining portion, and a third light inputted from the third input into the combining portion into combined light outputted from the output; the combining portion comprises two dichroic reflective surfaces; the combining portion is configured to pass a first passing wavelength band of the first light and to block the first light of a wavelength range outside the first passing wavelength band; the combining portion is configured to pass a second passing wavelength band of the second light and to block the second light of a wavelength range outside the second passing wavelength band; the combining portion is configured to block the first passing wavelength band of the third light, to block the second passing wavelength band of the third light, and to pass the third light of a wavelength range outside the first and second passing wavelength bands; the first passing wavelength band does not overlap with the second passing wavelength band; and the illumination apparatus further comprises a first light source arranged to input the first light into the first input of the beam combiner; a second light source arranged to input the second light into the second input of the beam combiner; a third light source arranged to input the third light into the third input of the beam combiner; wherein the first light comprises at least a part of the first passing wavelength band; the second light comprises at least a part of the second passing wavelength band; and at least one of the following conditions is satisfied: a combination of the second light passing through the combining portion and the third light passing through the combining portion is closer to the white point according to CIE1931 than each of the second light passing through the combining portion and the first light passing through the combining portion; and the third light passing through the combining portion is closer to the white point according to CIE1931 than each of the second light passing through the combining portion and the first light passing through the combining portion.

Thus, a higher flexibility in vascular imaging may be obtained. Namely, it allows true RGB illumination by whitish light which is closer to white than the standard green wide illumination in vascular enhanced imaging. Thus, the tissue may be observed by more natural colors.

BRIEF DESCRIPTION OF THE DRAWINGS

FIG. 7 shows schematically a reflectance spectrum of the crosscube, emission spectra of the first to third lights, and the spectrum of the combined light according to some embodiments of the invention;

DETAILED DESCRIPTION OF CERTAIN EMBODIMENTS

Figure 4:
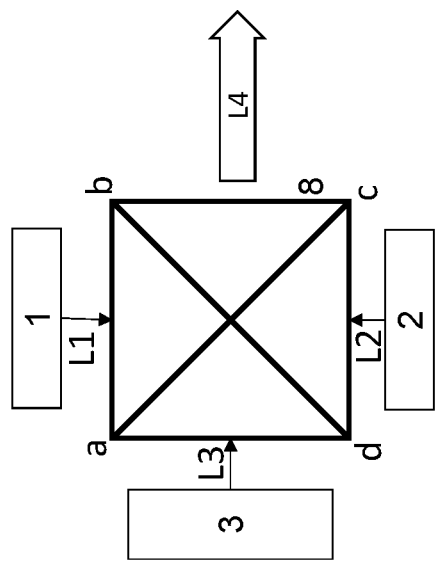
FIG. 4 shows schematically a plan view on an illumination apparatus according to some embodiments of the invention.

According to some embodiments of the invention, as shown in the plan view of FIG. 4, the illumination apparatus comprises three light sources 1, 2, and 3, and the lights from the three light sources are combined by a dichroic combiner, such as a crosscube 8. Light sources 1 and 2 may correspond to the narrowband light sources of conventional vascular imaging (i.e. a violet or ultraviolet light source emitting V light and a green wide light source Gw). The third light source 3 emits light such that, if the combiner combines the lights from the Gw light source and the third light source, the combined light is closer to the white point (x=y=z=⅓) of CIE 1931 than the Gw light alone passing through the dichroic combiner and the V light alone passing through the dichroic combiner. For example, the third light source may emit red light; or blue light; or red and blue light; or red, green, and blue light. In some embodiments, the light from the third light source alone, if transmitted through the dichroic combiner, may be closer to the white point than the light from the Gw light source alone passing through the dichroic combiner and the light from the V light source alone passing through the dichroic combiner.

Figure 6:
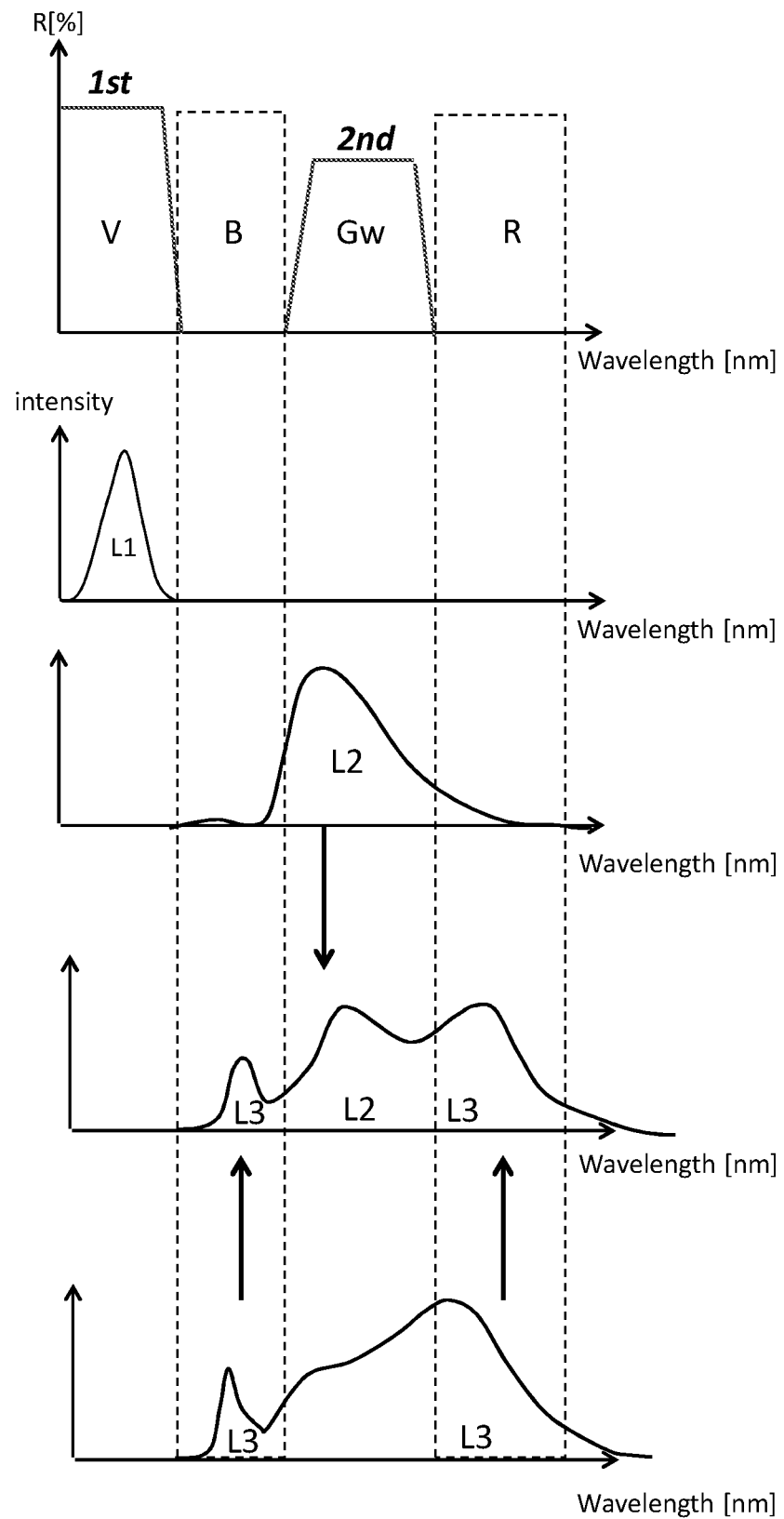
FIG. 6 (top) shows schematically a reflectance spectrum of the crosscube used in some embodiments of the invention, and the remainder of FIG. 6 shows light emission spectra of example LEDs that may be used as first to third light sources and a spectrum of a whitish output light.

An example of the combined light (illumination spectrum) emitted by the illumination apparatus is shown in FIG. 6 (last but one spectrum from bottom), for a case that the three light sources 1, 2, and 3 are switched on. As shown in FIG. 6, the V light and the Gw light may be the same as according to the prior art. The third light source 3 contributes additionally blue and/or red (amber) light to the combined light. Thus, the visible spectrum comprises RGB light (or BG light), which is typically closer to the white point than the green wide Gw light alone. Accordingly, the doctor can observe the tissue in more natural colors than with the conventional illumination system.

In the present application, the term "closer to the white point" means a shorter Euklidian distance in the x-y-plane of the gamut of CIE1931 from the white point x=y=⅓ (the z-direction is ignored). The Euklidian distance of an illumination light with coordinates $x_i$, $y_i$ in the x-y-plane from the white point is $(x_i-\frac{1}{3})^2+(y_i-\frac{1}{3})^2$.

Hereinafter, embodiments of the illumination apparatus are described at greater detail.

FIG. 4 shows an overview of the illumination apparatus in plan view. Three light sources 1, 2, and 3 are arranged such that they illuminate the first input face, second input face, and third input face of a crosscube 8 with first light L1, second light L2, and third light L3, respectively. Each of the light sources 1, 2, and 3 may comprise a respective LED, laser, or another light emitting device. Each of the light sources 1, 2, and 3 may or may not comprise one or more lenses, mirrors, or other optical components to guide the respective light to the respective input face of the crosscube 8. Each of the light sources 1, 2, and 3 may be controllable independently from the others of the light sources 1, 2, and 3. E.g., each of the light sources 1, 2, and 3 may be switched on and off independently from the other light sources. In some embodiments, in addition, the intensities of some of the light sources may be controlled independently.

Figure 5:
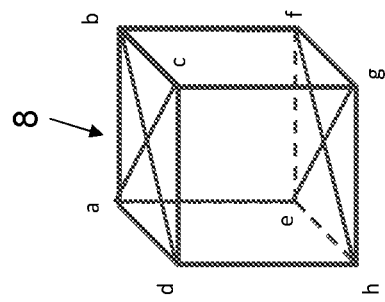
FIG. 5 shows a three-dimensional view of the crosscube used in some embodiments of the invention.

FIG. 5 shows a three-dimensional view of the crosscube 8. Small letters a to h denote the corners of the crosscube. The crosscube comprises a first dichroic reflective surface a-c-g-e and a second dichroic reflective surface b-f-h-d. In the plan view on the crosscube 8 shown in FIG. 4, the sections a-c and b-d of the dichroic reflective surfaces form the diagonals of the square forming the upper surface of the cross cube. In some embodiments, the combining portion of the crosscube consists of the first and second dichroic reflective surfaces.

The input faces are three outer side surfaces of the crosscube. Namely, the first input face is the side surface a-b-e-f, the second input face is the side surface c-g-h-d, and the third input face is the side surface a-e-h-d. The first input face is opposite to the second input face, and the third input face connects the first and second input faces.

The combined light L4 is emitted from the output face b-f-g-c. The output face is opposite to the third input face and connects the first and second input faces.

Each of the first and second dichroic reflective surfaces reflects a respective wavelength band and transmits light of a wavelength band outside the reflected wavelength band. Preferably, one or both of the dichroic reflective surfaces transmit all visible wavelengths outside the respective reflected wavelength band.

FIG. 6 (top) shows schematically a reflectance spectrum of the crosscube X. The first dichroic reflective surface reflects V light, and the second dichroic reflective surface reflects Gw light. The reflectances of the dichroic reflective surfaces may be the same or different from each other, as shown in FIG. 6.

The remainder of FIG. 6 shows schematically the corresponding light intensities from the light sources according to an embodiment of the invention. The light sources may be, for example:

light source 1 (L1, Violet): $2^{nd}$ diagram from top (e.g. NVSU233B-U405 of Nichia Corporation);
light source 2 (L2, Green): $3^{rd}$ diagram from top (e.g. NCSGE17AT of Nichia Corporation); and
light source 3 (L3, Other): diagram on the bottom (e.g. NF2L757GRT-V1 of Nichia Corporation.

The spectrum on the $2^{nd}$ diagram from the bottom of FIG. 6 shows the output light when both L2 and L3 are switched on. As may be seen, the combined light comprises R, G, and B light such that it is closer to the white point of CIE1931 than the spectrum of L2 alone.

FIG. 7 shows additionally to a reflectance spectrum of the crosscube schematically the wavelength ranges of the $1^{st}$ to $3^{rd}$ emitted lights L1, L2, and L3 and the resulting combined light L4. For simplicity, the edges of the reflectance spectra in FIG. 7 are sharp, and it is assumed that the reflectance is either 100% or 0%. Furthermore, FIG. 7 only indicates the wavelength ranges where the first to third lights L1 to L3 are emitted, ignoring any intensity dependency from the wavelength. If these simplifications are not valid, the resulting combined light L4 is obtained by a convolution of the reflectance spectrum (for the first and second lights L1 and L2) or the transmission spectrum (for the third light L3) and the light intensities.

The first dichroic reflective surface a-c-g-e reflects light of a first passing wavelength band (e.g. violet and/or ultraviolet light; denoted as $1^{st}$ in FIG. 6) input into the first input face such that it exits from the output face, and it transmits the other visible wavelengths. The first light source 1 emits violet and/or ultraviolet light L1. The emission spectrum of the first light source 1 and the reflection spectrum of the first dichroic reflective surface a-c-g-e overlap.

Thus, if the first light source 1 emits the first light L1 to the first input face a-b-e-f, the combined light L4 comprises violet and/or ultraviolet light of the overlapping wavelength range. For example, this light may be V light from conventional vascular imaging or different therefrom. First light L1 from the first light source 1 of wavelengths different from the reflection spectrum of the first dichroic reflective surface (first passing wavelength band) is transmitted through the first dichroic reflective surface such that it does not contribute to the output light L4.

The second dichroic reflective surface b-f-h-d reflects light of a second passing wavelength band (e.g. green light; denoted as $2^{nd}$ in FIG. 6) input into the second input face such that it exits from the output face, and it transmits the other visible wavelengths. The second light source 2 emits green light or green wide light L2. The emission spectrum of the second light source 2 and the reflection spectrum of the second dichroic reflective surface b-f-h-d overlap. Thus, if the second light source 2 emits the second light L2 to the second input face c-g-h-d, the combined light L4 comprises green or green wide light of the overlapping wavelength range. For example, this light may be Gw light from conventional vascular imaging or different therefrom. Second light L2 from the second light source 2 of wavelengths different from the reflection spectrum of the second dichroic reflective surface (second passing wavelength band) is transmitted through the second dichroic reflective surface such that it does not contribute to the output light L4. The first passing wavelength band and the second passing wavelength band do not overlap.

The third light L3 emitted by the third light source 3 is transmitted through both the first dichroic reflective surface a-c-g-e and the second dichroic reflective surface b-f-h-d in order to contribute to the combined light L4. Accordingly, the third light source 3 contributes to the combined light L4 by its emitted third light 3 from which the light of the first passing wavelength band and the light of the second passing wavelength band are blocked.

In the example of FIG. 7, the wavelength range of the first light L1 is larger than the first passing wavelength band (first reflectance wavelength band) of the first dichroic reflective surface. The combined light L4 comprises only the contributions of the first light L1 within the passing wavelength band. Since none of the other lights L2 and L3 is emitted in the wavelength range exceeding the first passing wavelength band, the combined light L4 has a gap 12 in this wavelength range.

The second passing wavelength band (second reflectance wavelength band) of the second dichroic reflective surface extends farther to the long wavelength side than the emission spectrum of the second light L2. The crosscube does not pass the third light L3 through the reflectance wavelength band of the second dichroic reflective surface. Hence, the combined light L4 has a gap 13 in this wavelength range.

In the wavelength range 15, the second light L2 is transmitted by the second dichroic reflective surface. Therefore, the second light L2 does not contribute to the combined light L4 in this wavelength range 15. On the other hand, the third light L3 comprises the wavelength range 15, too. It passes (is transmitted) through both the first and the second dichroic reflective surfaces such that it contributes to the combined light L4 in the wavelength range 15.

On the other hand, in the wavelength range 16, only the second light L2 contributes to the combined light L4 because, in the wavelength range 16, the third light L3 is reflected by the second dichroic reflective surface such that it does not exit from the output face.

FIG. 7 shows an example of the reflectance wavelength bands and the corresponding emission wavelength bands. This example is not limiting. For example, one or more of the emission wavelength ranges may be smaller than the corresponding reflectance wavelength band. The third light may have a gap in its emission spectrum, preferably in the second reflectance wavelength band. The third light may an emission spectrum on only one side of the second reflectance wavelength band. The reflectance wavelength bands and the corresponding emission wavelength bands may be arranged such that the wavelength range of the combined light L4 does not have any gap or any number of gaps.

Typically, the first and second light sources 1 and 2 comprise two narrowband light sources such as a violet light source (LED or laser) and a green (or green wide) light source (LED or laser). The third light source 3 is typically a wideband light source such as a white (or whitish) light source. The whitish light source may be phosphor covered LEDs (or lasers), wherein the phosphor converts a part of the blue/violet/ultraviolet light emitted by the LED (laser) into light of a longer wavelength.

Figure 9:
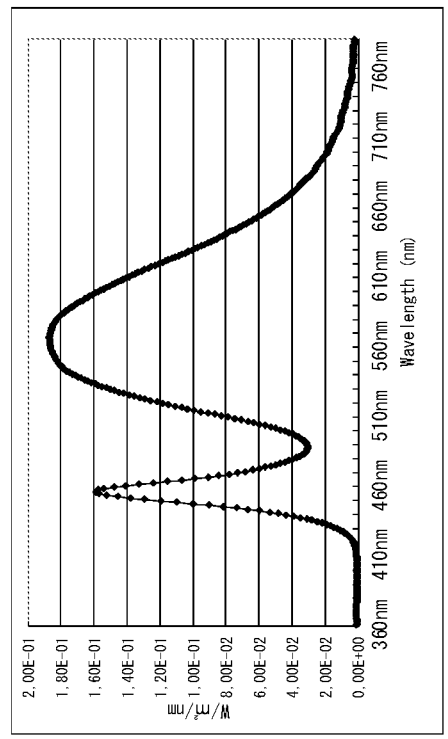
FIG. 9 shows an emission spectrum of the LED of FIG. 8 covered by the yellow phosphor on which a dome reflector lens is applied, deployed in some embodiments of the invention as a Gw light source.
Figure 8:
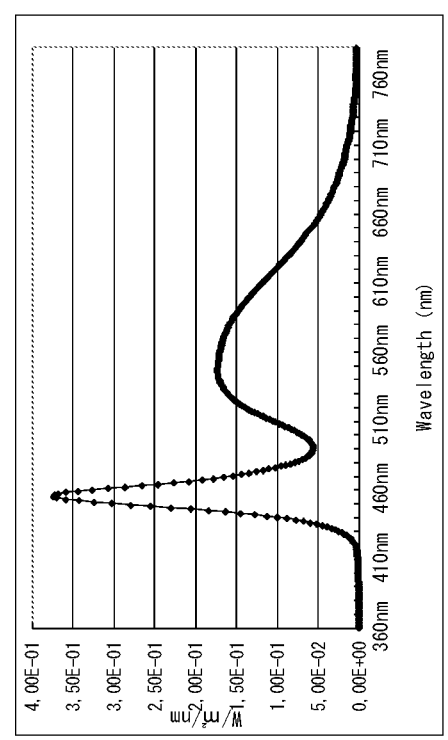
FIG. 8 shows an emission spectrum of a yellow phosphor covered LED that may be deployed in some embodiments of the invention as a Gw light source.

FIGS. 8 and 9 show some emission spectra of example LEDs that may be used as the green (green wide) light source (L2 in FIGS. 4 and 6). FIG. 8 shows an emission spectrum of a phosphor covered white LED which may be used as a Gw light source. However, it is preferable to use this LED with a dome reflector lens, as shown in FIG. 9 and explained in DE 11 2018 003134 T5 (FIGS. 11 and 12). Namely, the light from the white LED not passing directly through the opening of the dome reflector lens is reflected several times between the dome reflector lens and the LED, each time passing through the phosphor, before it finally passes through the opening of the dome reflector lens to the outside. Thus, the proportion of the green fluorescence light is enhanced in the output light.

Figure 10:
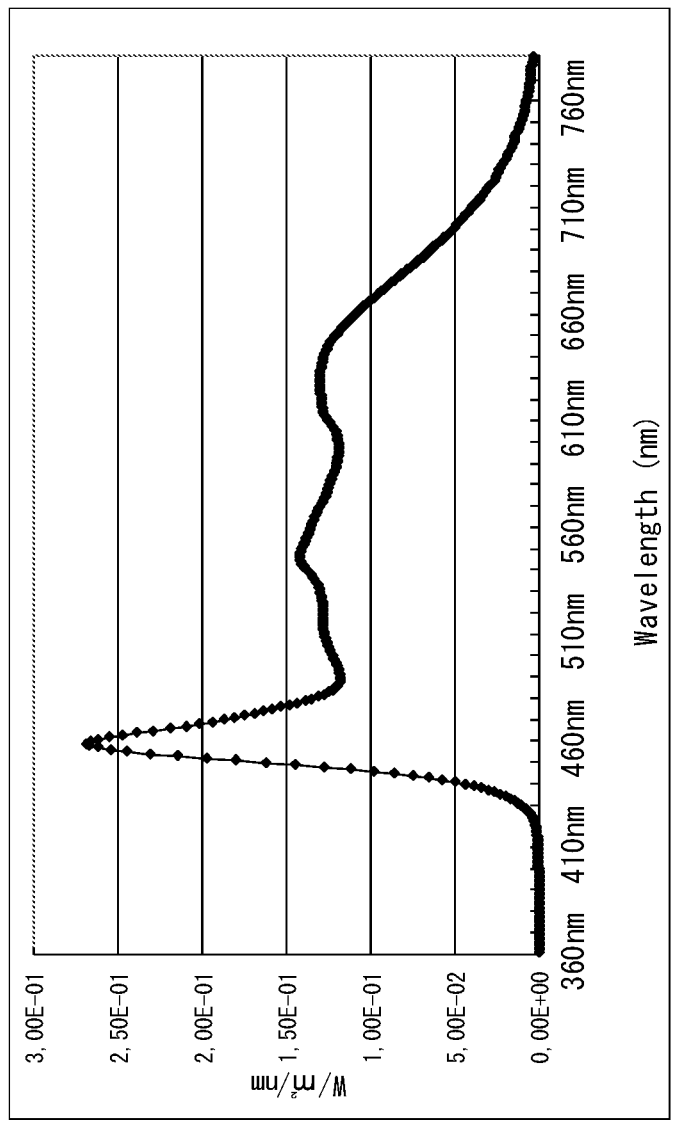
FIG. 10 shows an emission spectrum of a LED that may be deployed in some embodiments of the invention as a whitish light source.

FIG. 10 shows an emission spectrum of another example LED that may be used as the white light source (L3 in FIGS. 4 and 6). In this case, the LED is covered with a mixture of red and green phosphor.

In some embodiments, one of the narrowband light sources (e.g. the second light source 2 emitting green light) emits such a broad spectrum of green light that it appears as whitish with a green hue. On the other hand, the third light source 3 may emit the complementary colors to the second light source, i.e. red and blue light. Thus, the combined light comprises RGB.

Figure 1:
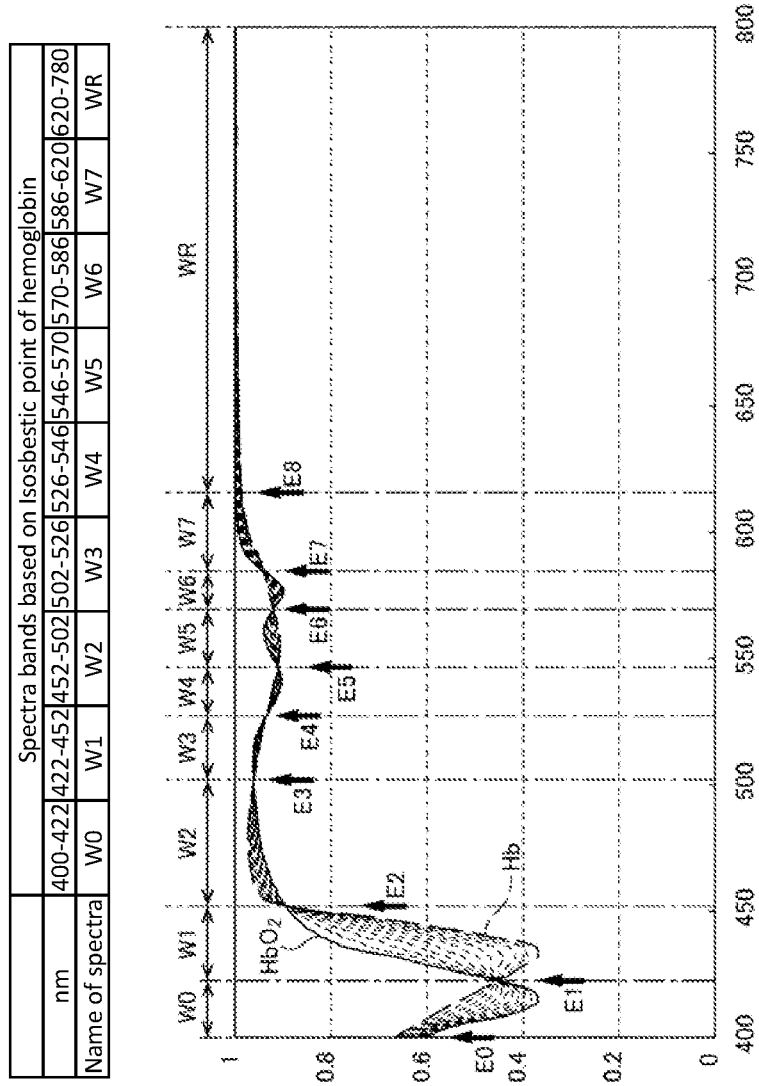
FIG. 1 shows absorption spectra of Hb and HbO2 with the isosbestic points.
Figure 2:
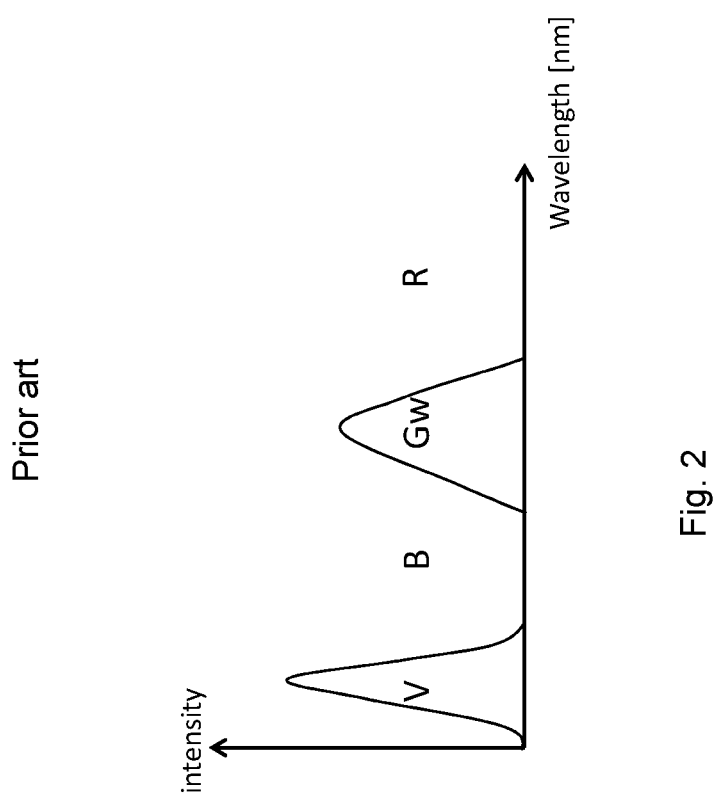
FIG. 2 shows schematically a conventional illumination spectrum for vascular imaging.
Figure 3:
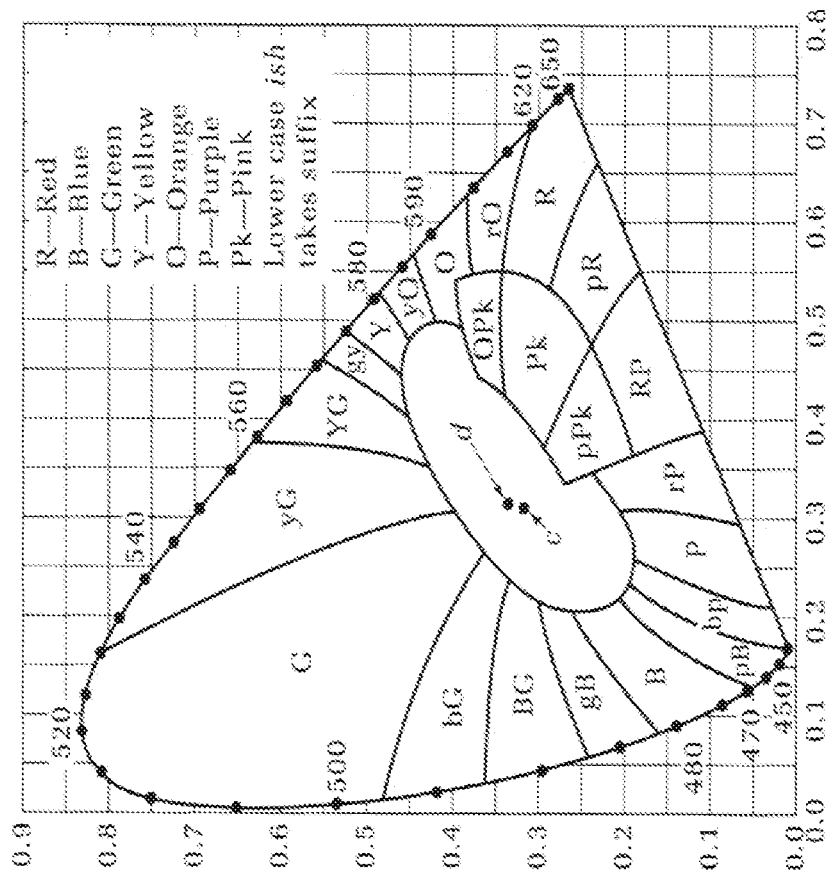
FIG. 3 shows a gamut according to CIE 1931.

Table 1 shows some examples of reflection bands of the dichroic reflective surfaces. These reflection bands are selected in view of the isosbestic points of Hb and HbO2 shown in FIG. 1. W1 to W6 denote the wavelength ranges correspondingly denoted in FIG. 1. The third light outside the indicated bands may pass through the crosscube to contribute to the combined light.

TABLE 1

Preferred reflectance bands of the first and second dichroic reflective surfaces for vascular imaging

| Reflection band | first dichroic reflective surface | second dichroic reflective surface |
|---|---|---|
| Description | W0 to W2<br>All of them; or<br>2 of them (preferred W0 + W1); or<br>1 of them (preferred W0 or W1, but not W2) | W3 to W6<br>All of them; or<br>3 of them (preferred W3 to W5 or W4 to W6); or<br>2 of them (preferred W3 + W4 or W4 + W5 or W5 + W6 (W4 + W5 or W5 + W6 is more preferred)); or<br>W5 |

The wavelength ranges of the colors described hereinabove are or example within the following ranges:

Violet or ultraviolet: 380-450 nm.
Blue: 450-495 nm.
Green: 495-570 nm.
Yellow: 570-590 nm.
Orange: 590-620 nm (sometimes also called amber).
Red: 620-750 nm.

Visible light is assumed to cover the wavelength range 400-750 nm.

It is sufficient if a major portion of the light intensity is emitted/reflected/transmitted in the indicated wavelength range. The light may or may not comprise further components outside the indicated wavelength ranges.

Some embodiments of the invention are described as if the dichroic reflective surfaces fully reflect a respective passing wavelength band (reflectance=100%) and fully transmit wavelengths outside the respective passing wavelength band (transmittance=100%). However, in some embodiments, the reflectance may be smaller than 100%. For example, it may be larger than 60%, preferably larger than 80%. Correspondingly, in some embodiments, the transmittance may be smaller than 100%. For example, it may be larger than 60%, preferably larger than 80%.

Some embodiments of the invention are described, wherein the lights are combined by a crosscube. However, the invention is not limited to a crosscube to combine the lights. Instead, two dichroic mirrors may be used having spectral reflectances corresponding to the dichroic reflective surfaces of the crosscube. The two dichroic mirrors are arranged one after the other. In the first dichroic mirror, two of the first to third lights are combined, and in the second dichroic mirror, the combined light from the first dichroic mirror is combined with the remaining light of the first to third light.

In some embodiments, even more than three lights are combined. For example, the combined light from a crosscube (or from two dichroic mirrors) is combined with a fourth light by a (further) dichroic mirror, or it is combined with a fourth light and a fifth light by a (further) crosscube etc. Also, the crosscube may comprise one or two further dichroic reflective surfaces. In the perspective view of FIG. 5, these further dichroic reflective surfaces may be arranged such that they reflect light entering the top and bottom face of the crosscube to the output face (surfaces a-f-g-d and h-e-b-c). The reflective bands of these further dichroic reflective surfaces does not overlap with each other and with those of the other dichroic reflective surfaces.

Instead of a crosscube, a crossprism may be used, wherein at least one of the side lengths is different from the other side lengths, and/or wherein at least one of the edges does not form a right angle.

According to some embodiments of the invention, the illumination apparatus may not comprise any movable parts. In particular, the reflective dichroic surfaces may not be movable relative to each other, relative to the input faces, or relative to the light sources. This facilitates the setup and reduces the maintenance effort.

The illumination system according to some embodiments of the invention may be arranged in an external box (light source box or processor system). The light from the external box may be guided from the proximal end of the endoscope to the distal end of the endoscope through one or more optical fibers in order to illuminate an object space of an objective lens arranged at the distal end of the endoscope. However, the light source may be arranged in a control body, an endoscope connector, or even in the distal tip of an endoscope instead.

In some embodiments, the optical fiber and optics to direct the light from the crosscube into the optical fiber may be considered as belonging to the output of the illumination apparatus. In these embodiments, their influence on the light output from the crosscube may be taken into account when designing the light sources and the dichroic reflective interfaces.

The endoscope comprising the illumination apparatus may be a capsule endoscope without a shaft (e.g. flexible tube) or an endoscope comprising a rigid tip portion and a shaft (e.g. rigid or flexible tube). The rigid tip portion may be connected to the shaft directly or indirectly via an angulation segment.

The illumination apparatus according to some embodiments of the invention may be used outside an endoscope, if at least two colored illumination lights and white (or substantially white) illumination light are required or desired. Depending on the substance to be observed, the colored light sources may emit different colors than violet (or ultraviolet) light and green (or green wide) light. For example, some fluorescence imaging agents can be applied, such as 5-ALA, which has absorption peak wavelength at 405 nm, and the reflection bands of the dichroic mirror may be accordingly adapted.

The invention claimed is:

1. An illumination apparatus, comprising
a beam combiner comprising first, second, and third inputs, a combining portion, and an output; wherein
the combining portion is configured to combine a first light inputted from the first input into the combining portion, a second light inputted from the second input into the combining portion, and a third light inputted from the third input into the combining portion into combined light outputted from the output;
the combining portion comprises two dichroic reflective surfaces;
the combining portion is configured to pass a first passing wavelength band of the first light and to block the first light of a wavelength range outside the first passing wavelength band;
the combining portion is configured to pass a second passing wavelength band of the second light and to block the second light of a wavelength range outside the second passing wavelength band;

the combining portion is configured to block the first passing wavelength band of the third light, to block the second passing wavelength band of the third light, and to pass the third light of a wavelength range outside the first and second passing wavelength bands;

the first passing wavelength band does not overlap with the second passing wavelength band; and the illumination apparatus further comprises a first light source arranged to input the first light into the first input of the beam combiner;

a second light source arranged to input the second light into the second input of the beam combiner;

a third light source arranged to input the third light into the third input of the beam combiner; wherein the first light including a wavelength of at least one of violet and ultraviolet comprises at least a part of the first passing wavelength band; the second light including a wavelength of green comprises at least a part of the second passing wavelength band; and the third light including wavelengths of red and blue passing through the combining portion is closer to the white point according to CIE1931 than each of the second light passing through the combining portion and the first light passing through the combining portion.

2. The illumination apparatus according to claim 1, wherein each of the first to third light sources is separately controllable.

3. The illumination apparatus according to claim 1, wherein the combining portion is one of
a pair of dichroic mirrors; and
a crossprism with two dichroic interfaces.

4. The illumination apparatus according to claim 1, wherein at least one of the first to third light sources is a light emitting diode or a laser diode.

5. The illumination apparatus according to claim 1, wherein at least one of
the two dichroic reflective surfaces are not mechanically movable relative to each other, and
the two dichroic reflective surfaces are not mechanically movable relative to the first to third inputs and to the output.

6. A rigid tip portion of an endoscope or a capsule endoscope for inserting into a lumen of a human body, comprising an objective lens and the illumination apparatus according to claim 1 arranged to illuminate by the combined light at least a portion of an object space imaged by the objective lens.

7. An endoscope comprising the rigid tip portion according to claim 6 and a shaft for inserting into the lumen of the human body, wherein the rigid tip portion is directly or indirectly connected to the shaft.

8. The illumination apparatus according to claim 1, wherein a combination of the second light passing through the combining portion and the third light passing through the combining portion is closer to the white point according to CIE1931 than each of the second light passing through the combining portion and the first light passing through the combining portion.

* * * * *